US011801020B2

(12) United States Patent
Shige et al.

(10) Patent No.: US 11,801,020 B2
(45) Date of Patent: Oct. 31, 2023

(54) X-RAY DIAGNOSTIC APPARATUS, MARKER DETECTING METHOD, AND COMPUTER-READABLE NON-TRANSITORY RECORDING MEDIUM

(71) Applicant: CANON MEDICAL SYSTEMS CORPORATION, Otawara (JP)

(72) Inventors: Fumimasa Shige, Otawara (JP); Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 285 days.

(21) Appl. No.: 17/092,848

(22) Filed: Nov. 9, 2020

(65) Prior Publication Data

US 2021/0161485 A1 Jun. 3, 2021

(30) Foreign Application Priority Data

Nov. 29, 2019 (JP) ................................ 2019-216175

(51) Int. Cl.
*A61B 6/12* (2006.01)
*A61B 6/00* (2006.01)
(Continued)

(52) U.S. Cl.
CPC ............... *A61B 6/12* (2013.01); *A61B 6/463* (2013.01); *A61B 6/5229* (2013.01); *A61B 6/542* (2013.01);
(Continued)

(58) Field of Classification Search
CPC ..................................................... A61B 6/12
See application file for complete search history.

(56) References Cited

U.S. PATENT DOCUMENTS

| 7,792,342 B2 * | 9/2010 | Barbu ...................... A61B 6/12 382/128 |
| 2005/0129296 A1 * | 6/2005 | Setala ...................... G06T 7/75 382/131 |

(Continued)

FOREIGN PATENT DOCUMENTS

| JP | 2010-131371 A | 6/2010 |
| JP | 2011-156321 A | 8/2011 |

(Continued)

OTHER PUBLICATIONS

"Sales of PCI Suite, a Comprehensive System Solution of Live Image Guidance, for Supporting Endovascular Treatment Technique of Heart and Coronary Artery Diseases—Provided with Latest Functions containing Dynamic Coronary Roadmap and Live StentBoost," Philips Electronics Co., Ltd., Jun. 30, 2016 (with English Abstract), 10 pages.

(Continued)

*Primary Examiner* — Colin T. Sakamoto
(74) *Attorney, Agent, or Firm* — Oblon, McClelland, Maier & Neustadt, L.L.P.

(57) ABSTRACT

An X-ray diagnostic apparatus according to an embodiment includes an X-ray tube, an X-ray detector, image generating circuitry, and processing circuitry. The X-ray tube generates an X-ray. The X-ray detector is positioned in a manner facing the X-ray tube, and detects the X-ray. The image generating circuitry generates an X-ray image one after another, based on an output of the X-ray detector. The processing circuitry identifies an inserted object inside a subject in the X-ray image, by performing an image recognition process to the X-ray image. The processing circuitry sets the area to be searched for a marker, based on the inserted object identified in the X-ray image. The processing (Continued)

circuitry detects the marker in the X-ray image, by searching the area to be searched for the marker.

13 Claims, 9 Drawing Sheets

(51) Int. Cl.
G06V 10/141 (2022.01)
G06V 10/20 (2022.01)
G06V 20/52 (2022.01)
G06V 10/24 (2022.01)

(52) U.S. Cl.
CPC .......... *G06V 10/141* (2022.01); *G06V 10/255* (2022.01); *G06V 20/52* (2022.01); *A61B 6/4441* (2013.01); *A61B 6/5264* (2013.01); *G06V 10/245* (2022.01); *G06V 2201/034* (2022.01)

(56) References Cited

U.S. PATENT DOCUMENTS

2007/0280422 A1* 12/2007 Setala ................. A61B 6/5264
378/197
2008/0154122 A1* 6/2008 Vaillant .................... A61B 6/12
600/424
2010/0104167 A1 4/2010 Sakaguchi et al.
2011/0249790 A1* 10/2011 Bismuth ................ A61B 6/504
378/62
2014/0051991 A1 2/2014 Sakaguchi et al.
2017/0065235 A1 3/2017 Sakaguchi et al.
2018/0140260 A1 5/2018 Taguchi et al.
2018/0317865 A1 11/2018 Sakaguchi et al.
2019/0282304 A1* 9/2019 Sato ..................... A61B 6/5252
2020/0000420 A1 1/2020 Sakaguchi et al.
2020/0069263 A1 3/2020 Taguchi et al.

FOREIGN PATENT DOCUMENTS

JP 2016-120144 A 7/2016
JP 2018-82767 A 5/2018

OTHER PUBLICATIONS

Nambu, K. et al., "Renewing X ray Fluoroscopy," Progress in CI, vol. 32, No. 2, 2010 (with English Translation), 10 pages

* cited by examiner

| TYPE OF INSERTED OBJECT | AREA TO BE SEARCHED |
|---|---|
| CONTRAST AGENT | REGION NEAR PAST MARKER IN BLOOD VESSEL IMAGE |
| INFLATED BALLOON | REGIONS NEAR BOTH ENDS OF INFLATED BALLOON REGION IN CATHETER IMAGE |
| DEFLATED BALLOON | REGION NEAR WIRE IN CATHETER IMAGE |
| PLURALITY OF BALLOONS | REGION NEAR WIRE REGION RELATED TO DYNAMIC BALLOON IN CATHETER IMAGE |

X-RAY DIAGNOSTIC APPARATUS, MARKER DETECTING METHOD, AND COMPUTER-READABLE NON-TRANSITORY RECORDING MEDIUM

CROSS-REFERENCE TO RELATED APPLICATIONS

This application is based upon and claims the benefit of priority from Japanese Patent Application No. 2019-216175, filed on Nov. 29, 2019; the entire contents of which are incorporated herein by reference.

FIELD

Embodiments described herein relate generally to an X-ray diagnostic apparatus, a marker detecting method, and a computer-readable non-transitory recording medium.

BACKGROUND

As an intraoperative support for cardiac catheterization, there is a technology for displaying a stent, which moves with pulsations, in a manner fixed at the center of a screen. To fix the position of the stent at the center of the screen, markers associated with the balloon are detected from a fluoroscopic image, and a coordinate conversion is then performed based on the detected markers. The markers are detected by applying image processing that makes it easier to find markers, and then applying another image processing that detects markers in the image, based on such information as shape. Furthermore, a trained model has recently come to be used as a technology for detecting objects.

The markers associated with a balloon are thin and small. Therefore, the conventional image processing technique has a problem in that a bone, or a blood vessel having contrast agent may falsely be detected as a marker. In addition, a marker in a fluoroscopic image is represented as a dot only having a few pixels. Furthermore, there are not too many features inside or around a marker. For these reasons, it has been known that marker detections often result in false negatives or false positives. Furthermore, known as another conventional technology is an approach for detecting the movement of the markers at a single heartbeat first, and then narrowing down the area where the markers are to be searched, for example. However, the accuracy of this technique depends on the accuracy of the marker detection carried out at the first step. This processing still has a problem of low marker detection accuracy because the accuracy of the marker detection carried out at the first step has not been improved.

DETAILED DESCRIPTION

An X-ray diagnostic apparatus, a marker detecting method, and a computer-readable non-transitory recording medium according to an embodiment will now be explained in detail with reference to the drawings. In the embodiment described below, it is assumed that parts with the same reference numerals perform the same operations, and redundant explanations thereof will be omitted as appropriate. Note that the X-ray diagnostic apparatus disclosed herein is not limited to that described in the embodiment below.

The X-ray diagnostic apparatus explained in the embodiment includes an X-ray tube, an X-ray detector, image generating circuitry, and processing circuitry. The X-ray tube generates an X-ray. The X-ray detector is positioned in a manner facing the X-ray tube, and detects an X-ray. The image generating circuitry generates an X-ray image one after another, based on an output of the X-ray detector. The processing circuitry identifies an inserted object in a subject in the X-ray image, by performing an image recognition process to the X-ray image. The processing circuitry sets an area to be searched for a marker to the X-ray image, based on the identified inserted object. The processing circuitry detects the marker in the X-ray image, by searching the area to be searched for the marker.

EMBODIMENT

Figure 1:
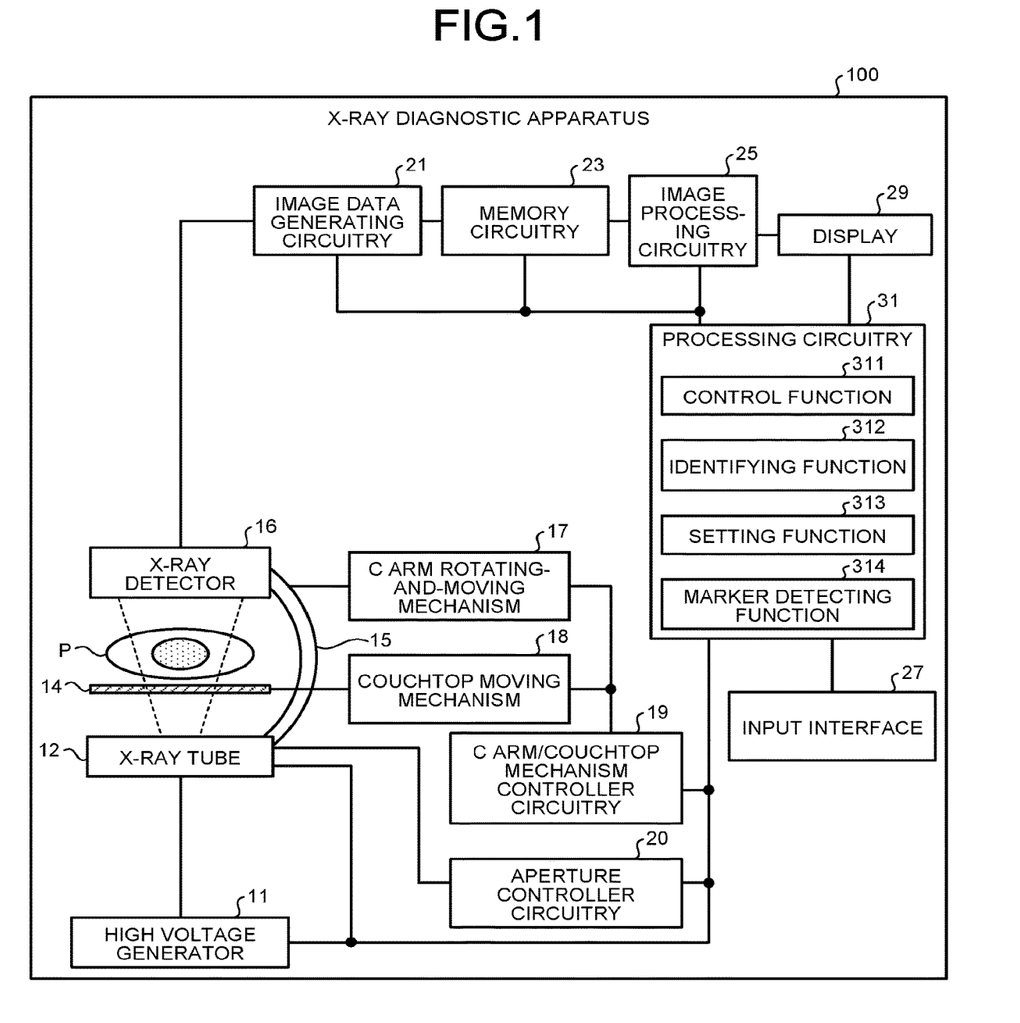
FIG. 1 is a schematic illustrating an exemplary configuration of an X-ray diagnostic apparatus according to an embodiment.

The overall configuration of an X-ray diagnostic apparatus according to the embodiment will now be explained. FIG. 1 is a schematic illustrating one example of a configuration of this X-ray diagnostic apparatus 100 according to the embodiment. As illustrated in FIG. 1, the X-ray diagnostic apparatus 100 includes a high voltage generator 11, an X-ray tube (bulb) 12, an X-ray aperture, a couchtop 14, a C arm (support) 15, an X-ray detector 16, a C arm rotating-and-moving mechanism 17, a couchtop moving mechanism 18, C arm/couchtop mechanism controller circuitry 19, aperture controller circuitry 20, image data generating circuitry 21, memory circuitry 23, image processing circuitry 25, an input interface 27, a display 29, and processing circuitry 31.

In the X-ray diagnostic apparatus 100 illustrated in FIG. 1, the processing functions are stored in the memory circuitry 23, as computer-executable programs. The C arm/couchtop mechanism controller circuitry 19, the aperture controller circuitry 20, the image data generating circuitry 21, the image processing circuitry 25, and the processing circuitry 31 are processors implementing functions corresponding to the computer programs, by reading the computer programs from the memory circuitry 23 and executing the computer programs. In other words, these circuitry having read the computer programs have the functions corresponding to the read computer programs.

The high voltage generator 11 generates a high voltage and a filament current, under the control of the processing circuitry 31. The high voltage generator 11 then applies the generated high voltage to the X-ray tube 12. The high voltage generator 11 supplies the filament current to the X-ray tube 12.

The X-ray tube 12 receives the application of the high voltage and the supply of the filament current from the high voltage generator 11, and emits thermal electrons from the cathode (filament) toward the anode (target). As a result, the X-ray tube 12 generates an X-ray. The quantity of thermal electrons travelling from the filament to the target, that is, a tube current is adjusted by controlling the filament current with the high voltage generator 11.

The X-ray aperture focuses the X-ray generated by the X-ray tube 12 so that the region of interest on the subject P is selectively irradiated with the X-ray, under the control of the aperture controller circuitry 20. The X-ray aperture has four slidable aperture blades, for example. The shape, the size, and the position of the opening of the X-ray aperture are changed discretionally by causing the aperture blades to be slid under the control of the aperture controller circuitry 20. By causing the X-ray aperture to adjust the size and the position of the opening, the size and the position of the area irradiated with X-ray on the detecting surface of the X-ray detector 16 are adjusted. In other words, the X-ray generated by the X-ray tube 12 is focused with the opening of the X-ray aperture, and the subject P is irradiated therewith.

The X-ray aperture is also provided with a plurality of additional filters for adjusting radiation quality. One of the additional filters is set depending on the examination, for example. These additional filters are changed under the control of the processing circuitry 31.

The couchtop 14 is a bed where the subject P is laid, and is placed on top of a couch not illustrated. The subject P is not included in the X-ray diagnostic apparatus 100.

The X-ray detector 16 is positioned in a manner facing the X-ray tube 12, and detects the X-ray passed through the subject P. For example, the X-ray detector 16 has detecting elements that are arranged in a matrix-like shape. Each of the detecting elements converts the X-ray passed through the subject P into an electric signal, and accumulates the electric signal. The detecting elements then transmit the accumulated electric signals to image data generating circuitry 21.

The C arm 15 holds the X-ray tube 12, the X-ray aperture, and the X-ray detector 16. The C arm 15 is caused to rotate about the subject P laid on the couchtop 14, by a motor provided to the C arm rotating-and-moving mechanism 17. For example, the C arm 15 is supported by an arm not illustrated, in a manner rotatable about each of three orthogonal axes that are X, Y, and Z axes. The C arm 15 supports the X-ray detector 16 in a manner facing the X-ray tube 12 and the X-ray aperture. In the example illustrated in FIG. 1, the X-ray diagnostic apparatus 100 is a single-plane diagnostic apparatus, but the embodiment is not limited thereto, and may also be a biplane diagnostic apparatus, for example.

The C arm rotating-and-moving mechanism 17 is a mechanism for rotating and moving the C arm 15. The C arm rotating-and-moving mechanism 17 is also capable of changing the source-to-image distance (SID), which is the distance between the X-ray tube 12 and the X-ray detector 16. The C arm rotating-and-moving mechanism 17 is also capable of rotating the X-ray detector 16 held by the C arm 15.

The couchtop moving mechanism 18 is a mechanism for moving the couchtop 14. The couchtop moving mechanism 18 has a motor or an actuator for moving the couchtop 14 in the long-axis direction and the short-axis direction of the couchtop 14. The couchtop moving mechanism 18 also has a motor or an actuator for tilting the couchtop 14.

The C arm/couchtop mechanism controller circuitry 19 adjusts the rotation and the movement of the C arm 15, and the movement of the couchtop 14, by controlling the C arm rotating-and-moving mechanism 17 and the couchtop moving mechanism 18, under the control of the processing circuitry 31. For example, the C arm/couchtop mechanism controller circuitry 19 controls fluoroscopic imaging for collecting projection data at a predetermined frame rate, under the control of the processing circuitry 31.

The image data generating circuitry 21 generates the projection data using the electric signal converted from the X-ray by the X-ray detector 16. The image data generating circuitry 21 stores the generated projection data in the memory circuitry 23. For example, the image data generating circuitry 21 generates projection data by performing a current-to-voltage conversion, an analog-to-digital (A/D) conversion, and a parallel-to-serial conversion to the electric signals received from the X-ray detector 16.

The memory circuitry 23 receives the projection data generated by the image data generating circuitry 21, and stores therein the data. The memory circuitry 23 also stores therein computer programs corresponding to various functions to be read and executed by the circuitry illustrated in FIG. 1. To explain using one example, the memory circuitry 23 stores therein a computer program corresponding to a control function 311, a computer program corresponding to an identifying function 312, a computer program corresponding to a setting function 313, and a computer program corresponding to a marker detecting function 314 that are read and executed by the processing circuitry 31. The memory circuitry 23 may also be implemented as a storage device, such as a hard disk drive (HDD), a solid state drive (SSD), or an integrated circuit storage device, storing therein various types of information. The memory circuitry 23 may also be implemented not only as an HDD or an SSD but also as a driver device for reading and writing various types of information from and to a portable medium such as a compact disc (CD) or a digital versatile disc (DVD), or a flash memory, or from or to a semiconductor memory such as a random access memory (RAM).

The image processing circuitry 25 generates an X-ray image by performing various types of image processing to the projection data stored in the memory circuitry 23, under the control of the processing circuitry 31. Alternatively, the image processing circuitry 25 generates an X-ray image by acquiring the projection data directly from the image data generating circuitry 21, and performing various types of image processing to the acquired projection data, under the control of the processing circuitry 31. The image data generating circuitry 21 and the image processing circuitry 25 correspond to an image generating unit (the image generating circuitry). The image generating unit generates an X-ray image one after another, based on an output of the X-ray detector 16. The image processing circuitry 25 may store the X-ray image applied with the image processing in the memory circuitry 23. The image processing circuitry 25, for example, can perform various types of processing, using image processing filters, such as a moving average (smoothing) filter, a Gaussian filter, a median filter, a recursive filter, and a band-pass filter.

The input interface 27 is implemented as a trackball, a switch button, a mouse, a keyboard, a touchpad for making input operations by touching its operation surface, a touch screen that is an integration of a display screen and a touchpad, a contactless input circuit using an optical sensor, and an audio input circuit for performing various settings, and a foot switch for executing X-ray irradiations. The input interface 27 is connected to the processing circuitry 31. The input interface 27 converts an input operation received from an operator into an electric signal, and outputs the electric signal to the processing circuitry 31. The input interface 27 described herein is not limited to those having physical operation components, such as a mouse or a keyboard. An example of such an input interface also includes an electric signal processing circuit for receiving the electric signal corresponding to an input operation from an external input device that is provided separately from the apparatus, and for outputting the electric signal to the controller circuit.

The display (display unit) 29 displays a graphical user interface (GUI) for receiving instructions from the operator, or various images generated by the image processing circuitry 25. The display 29 also displays results of various types of processing performed by the processing circuitry 31. As some examples of the display 29, a liquid crystal display (LCD), a cathode ray tube (CRT) display, an organic electro luminescence display (OELD), a plasma display, and any other type of display can be used as appropriate.

The processing circuitry 31 controls the entire operation of the X-ray diagnostic apparatus 100 based on the electric signal corresponding to an input operation output from the input interface 27. For example, the processing circuitry 31 includes, as its hardware resources, a processor such as a central processing unit (CPU), a micro-processing unit (MPU), or a graphics processing unit (GPU), and memories such as a read-only memory (ROM) and a random access memory (RAM). The processing circuitry 31 executes the control function 311, the identifying function 312, the setting function 313, and the marker detecting function 314, by causing the processor to execute a computer program loaded onto the memory. The configuration of the control function 311, the identifying function 312, the setting function 313, and the marker detecting function 314 is not limited to the implementation in one processing circuit. It is also possible to implement the control function 311, the identifying function 312, the setting function 313, and the marker detecting function 314 by using a combination of a plurality of independent processors as the processing circuit, and by causing each of the processors to execute a corresponding computer program.

It is also possible for the processing circuitry 31 to be implemented as an application-specific integrated circuit (ASIC), a field-programmable gate array (FPGA), or another complex programmable logic device (CPLD) or simple programmable logic device (SPLD).

Specifically, the processing circuitry 31 executes various types of processing by reading a computer program corresponding to the control function 311 that controls the entire apparatus from the memory circuitry 23, and executing the computer program. For example, the processing circuitry 31 adjusts the voltage applied to the X-ray tube 12 and the filament current supplied to the X-ray tube 12 by causing the control function 311 to control the high voltage generator 11 in accordance with an instruction given by the operator, and received from the input interface 27. By adjusting the voltage and the current, the processing circuitry 31 controls the dose and the radiation quality of the X-ray with which the subject P is irradiated, and to turn ON or OFF the X-ray irradiation. The processing circuitry 31 also adjusts the rotation or the movement of the C arm 15, or the movement or the tilt of the couchtop 14, by controlling the C arm/couchtop mechanism controller circuitry 19 in accordance with an instruction given by the operator.

The processing circuitry 31 also adjusts the opening of the aperture blades provided to the X-ray aperture, by causing the control function 311 to control the aperture controller circuitry 20 in accordance with an instruction given by the operator. By adjusting the opening of the aperture blades, the processing circuitry 31 controls the region of the subject P to be irradiated with the X-ray. The processing circuitry 31 also controls a projection data generation process performed by the image data generating circuitry 21, image processing performed by the image processing circuitry 25, an analysis process, and the like, in accordance with instructions given by the operator. The processing circuitry 31 also controls the display 29 to display GUIs for receiving instructions from the operator, images stored in the memory circuitry 23, results of processing performed by the processing circuitry 31, and the like, onto the display 29. The processing circuitry 31 implementing the control function 311 is one example of a control unit.

The processing circuitry 31 identifies an inserted object inside the subject in an X-ray image, by causing the identifying function 312 to perform an image recognition process to the X-ray image. For example, the processing circuitry 31 identifies the type of the inserted object inside the subject P in the X-ray image, by performing an image recognition process or an object detection process to the X-ray image. To make the explanation more specific, types of the inserted object are explained to be contrast agent, an inflated balloon on the catheter (hereinafter, referred to as an inflated balloon), a deflated balloon on the catheter (hereinafter, referred to as a deflated balloon), or a plurality balloons corresponding to a plurality of catheters. The catheter has structures such as a catheter tube, a wire, a balloon, a chip at the tip, and two markers indicating the position of the balloon on the catheter.

For example, the processing circuitry 31 causes the identifying function 312 to calculate an average of pixel values, using the pixel values of the entire X-ray image. The processing circuitry 31 then compares the average with a threshold related to the contrast agent (hereinafter, referred to as a contrast agent threshold). The contrast agent threshold is stored in the memory circuitry 23 in advance. The contrast agent threshold may be an average of the pixel values of an X-ray image generated before the contrast agent is injected into the subject P. If the calculated average is greater than the contrast agent threshold, the processing circuitry 31 causes the identifying function 312 to identify that the type of the inserted object is contrast agent.

The processing circuitry 31 also identifies an inflated balloon, a deflated balloon, or a plurality of balloons in the X-ray image, as a type of the inserted object in the X-ray image, through an object recognition process or an object detection process performed in the identifying function 312. The object recognition process is a machine learning model, such as a deep neural network, related to object recognitions (hereinafter, referred to as an object recognition DNN), for example. The object detection process is a process that uses histograms-of-oriented-gradients (HOG) features, for example. To make the explanation more specific, it is assumed that, in the explanation below, the identifying function 312 uses an object recognition DNN.

The object recognition DNN corresponds to a classifier that classifies the types of inserted objects in the X-ray image. The object recognition DNN is trained in advance, using training data for recognizing the types of inserted objects in the X-ray image. The object recognition DNN is stored in the memory circuitry 23, for example. The processing circuitry 31 causes the identifying function 312 to input an X-ray image to the object recognition DNN. The object recognition DNN outputs a recognition result corresponding to an inflated balloon, a deflated balloon, or a plurality of balloons, as an inserted object type, for example. The object recognition DNN may detect the presence of contrast agent, as the type of the inserted object in the X-ray image. The processing circuitry 31 implementing the identifying function 312 is one example of an identifying unit.

The processing circuitry 31 causes the setting function 313 to set the area where the marker is to be searched, based on the inserted object identified in the X-ray image. For example, if the inserted object is identified as contrast agent, the processing circuitry 31 sets a region near a marker in a past X-ray image captured at the same cardiac phase as that of the X-ray image, as the area where the marker is to be searched, to a region excluding a branch section of a blood vessel and an overlapping section where blood vessels overlap each other in the direction in which the X-ray is projected, from a blood vessel region in the X-ray image. If the inserted object is identified as an inflated balloon, the processing circuitry 31 sets regions near both ends of the region corresponding to the inflated balloon, as the areas where the marker is to be searched. If the inserted object is identified as a deflated balloon, the processing circuitry 31 sets a region near the wire related to the deflated balloon, as the area where the marker is to be searched. If the inserted object is identified as a, the processing circuitry 31 set a region near the wire related to a dynamic balloon, among the identified plurality of balloons, as the area where the marker is to be searched.

For example, the processing circuitry 31 causes the setting function 313 to set the area where the marker of the inserted object is to be searched in the X-ray image, based on the type of the inserted object. Specifically, when the type of the inserted object is contrast agent, the processing circuitry 31 sets a region near a marker in a past X-ray image of the subject P, captured at the same cardiac phase as that of the X-ray image, as the area to be searched, to a region excluding a branch section of a blood vessel and an overlapping section where blood vessels overlap each other in the direction in which the X-ray is projected, from the blood vessel region in the X-ray image. When the type of the inserted object is an inflated balloon, the processing circuitry 31 causes the setting function 313 to set regions near both ends of the region corresponding to the balloon in the X-ray image, as the areas to be searched. When the type of the inserted object is a deflated balloon, the processing circuitry 31 causes the setting function 313 to set a region near the wire in the X-ray image, as the area to be searched. When the type of the inserted object is a plurality of balloons, the processing circuitry 31 causes the setting function 313 to set a region near the wire of a dynamic balloon in the X-ray image, as the area to be searched in the X-ray image. The processing circuitry 31 implementing the setting function 313 is one example of a setting unit.

The processing circuitry 31 causes the marker detecting function 314 to detect a marker in the X-ray image, by searching the area to be searched for the marker. The processing circuitry 31 implementing the marker detecting function 314 is one example of a marker detecting unit. The specific processes related to the identifying function 312, the setting function 313, and the marker detecting function 314 will be explained in a process of detecting a marker in the X-ray image (hereinafter, referred to as a marker detection process).

Figure 2:
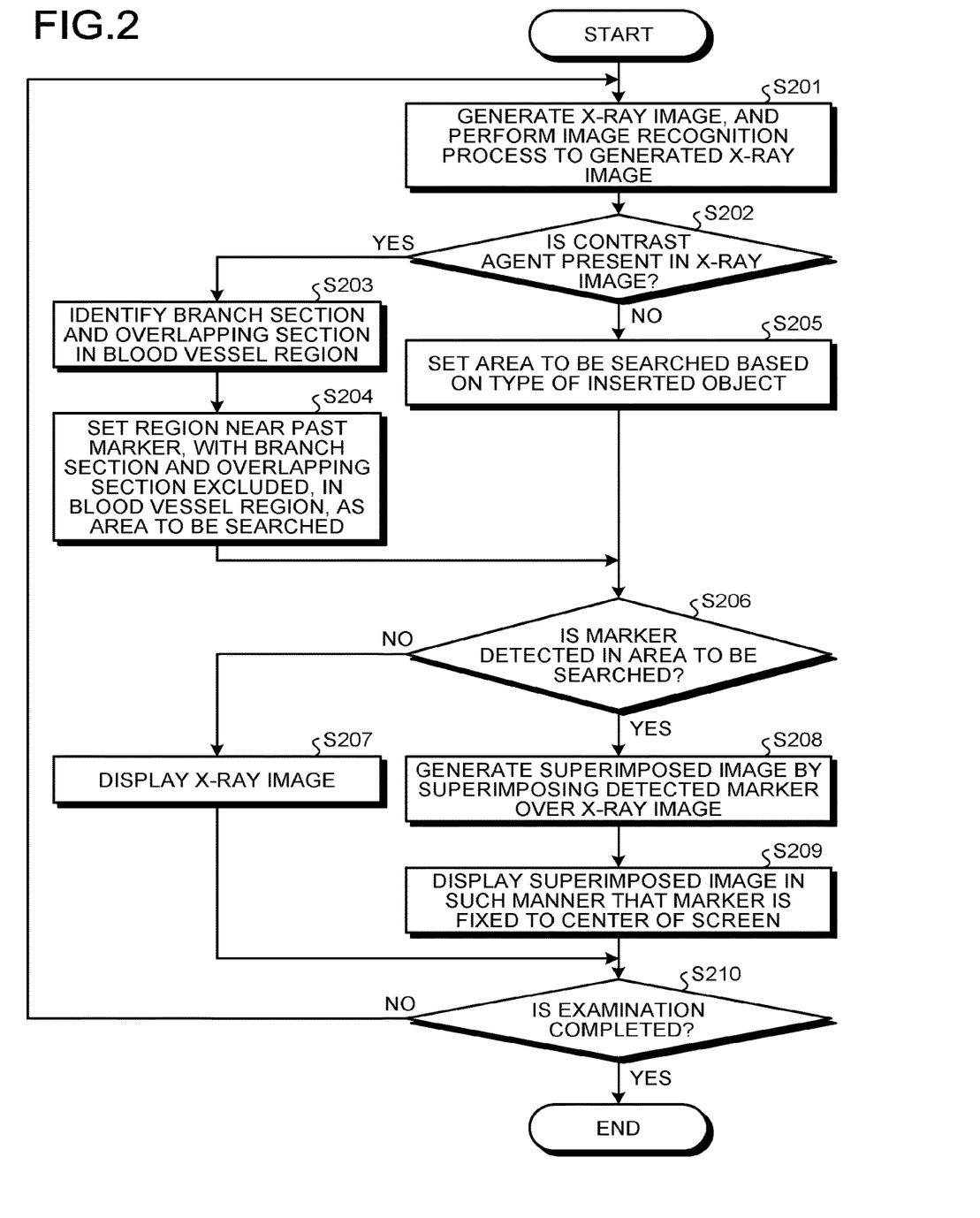
FIG. 2 is a schematic illustrating one example of the sequence of a marker detection process according to the embodiment.

The overall configuration of the X-ray diagnostic apparatus 100 has been explained above. The sequence of the marker detection process for improving the marker detection accuracy will now be explained. To make the explanation more specific, the explanation will be provided using an example in which a stent intervention treatment is to be performed to stenosis in the coronary artery of the subject P. The memory circuitry 23 stores therein a plurality of X-ray images obtained from a plurality of X-ray emissions to the subject P, that is, stores therein a plurality of fluoroscopic images. Furthermore, volume data generated by running X-ray computed tomography scans on the subject P may also be stored in the memory circuitry 23 in advance, before the intervention treatment is to be carried out. The memory circuitry 23 also stores therein a plurality of anatomical landmarks in the volume data, and a computer program (hereinafter, referred to as a 2D-3D aligning program) for executing alignment between a two-dimensional image and the volume data, using the anatomical landmarks. FIG. 2 is a schematic illustrating one example of the sequence of the marker detection process.

Marker Detection Process

Step S201

Figure 3:
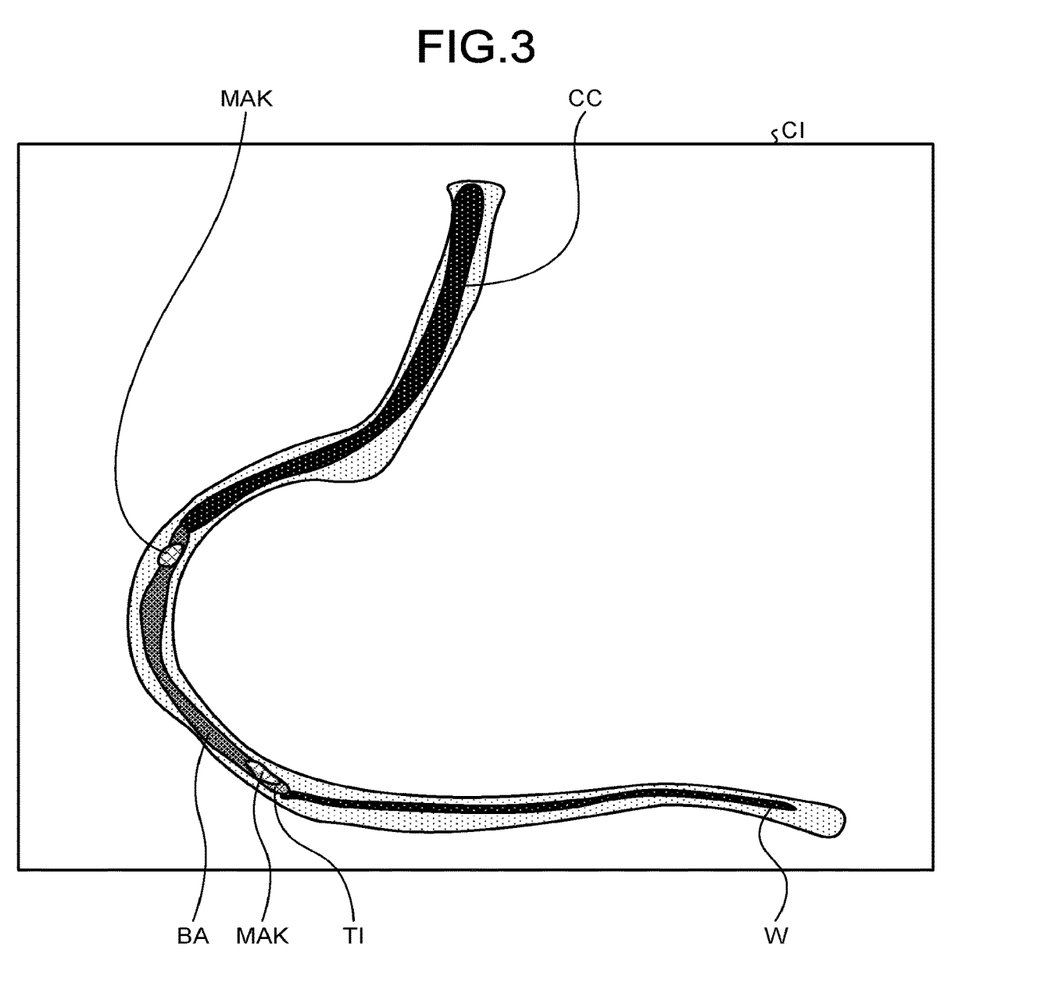
FIG. 3 is a schematic illustrating one example of a catheter image according to the embodiment.

The image processing circuitry 25 generates an X-ray image by irradiating the subject P with an X-ray. The processing circuitry 31 then causes the identifying function 312 to identify the type of the inserted object inside the subject P in the X-ray image. For example, the processing circuitry 31 identifies the presence of contrast agent, the presence of an inflated balloon, the presence of a deflated balloon, and the presence of a plurality of balloons, in the X-ray image, by causing the identifying function 312 to perform an image recognition process. If no contrast agent is identified in the X-ray image, the processing circuitry 31 identifies a region near the catheter including the region corresponding to the catheter in the X-ray image, by causing the identifying function 312 to perform an image recognition process. The processing circuitry 31 then generates an image (hereinafter, referred to as a catheter image) by substituting zero for the pixel values of the region other than the region near the catheter in the X-ray image, and having the same size as the X-ray image. FIG. 3 is a schematic illustrating one example of the catheter image CI. The catheter image includes a catheter tube CC, a wire W, a balloon BA, a chip-on-the-tip TI, and two markers MAK.

Step S202

As a result of the recognition performed by the identifying function 312, if the presence of the contrast agent is identified in the X-ray image (Yes at Step S202), the process at Step S203 is performed. At this time, the display 29 may display the detection of the contrast agent. It is also possible to allow the operator to enter an instruction for releasing the detection of the contrast agent via the input interface 27. This configuration allows the operator to make a correction in the detected contrast agent even if the identifying function 312 has detected the contrast agent falsely, so that marker detection accuracy is improved. After Yes at Step S202, the process at Step S203 is performed. As a result of the recognition performed by the identifying function 312, if the presence of contrast agent is not identified in the X-ray image (No at Step S202), the process at Step S203 is performed.

Step S203

The processing circuitry 31 then causes the identifying function 312 to extract a blood vessel region from the X-ray image. For example, the processing circuitry 31 identifies a blood vessel region by making a threshold determination of the X-ray image against a contrast agent threshold, or by applying an image recognition process to the X-ray image. The processing circuitry 31 also performs alignment between the X-ray image and the volume data, using the 2D-3D alignment program and the anatomical landmarks (that is, anatomical knowledge). In this manner, the processing circuitry 31 causes the identifying function 312 to identify a branch section of a blood vessel in the blood vessel region, and an overlapping section where blood vessels overlap each other in the direction in which the X-ray is projected, in the blood vessel region. The processing circuitry 31 may also identify the branch section and the overlapping section in the blood vessel region using a trained model that receives the X-ray image as an input, and outputs the branch section and the overlapping section. The processing circuitry 31 may also identify the branch section and the overlapping section in the blood vessel region by performing a segmentation process using thresholds of pixel values that are related to extractions of a branch section and an overlapping section. The processing circuitry 31 may also identify the branch section and the overlapping section by applying a pattern matching to the blood vessel region with the shapes of the branch sections and the shapes of the overlapping sections, these shapes being stored in the memory circuitry 23 in advance. In these cases, the 2D-3D aligning program, the anatomical landmarks, and the volume data are not necessary.

Step S204

The memory circuitry 23 also stores therein a marker (hereinafter, referred to as a past marker) in a past X-ray image (hereinafter, referred to as a past image) captured at the same cardiac phase as that of the X-ray image. The past marker corresponds to a marker detected at Step S206, which will be described later, in the past image. The processing circuitry 31 causes the setting function 313 to read the past marker from the memory circuitry 23. The processing circuitry 31 sets the region near the past marker, with the branch section and the overlapping section excluded, in the blood vessel region, as the area to be searched. Specifically, the processing circuitry 31 causes the setting function 313 to generate an image, that is, a blood vessel image by substituting zero for the pixel values of the region other than the blood vessel region, and for the pixel values of the branch section and the overlapping section in the X-ray image, in the same size as the X-ray image. The processing circuitry 31 then sets the region near the past marker in the generated blood vessel image, as the area to be searched.

Step S205

The processing circuitry 31 causes the setting function 313 to set the area where the marker of the inserted object is to be searched, based on the type of the inserted object. For example, when the type of the inserted object is an inflated balloon, the processing circuitry 31 causes the identifying function 312 to identify the balloon region in the catheter image. The balloon region corresponds to the region BA in FIG. 3.

Figure 4:
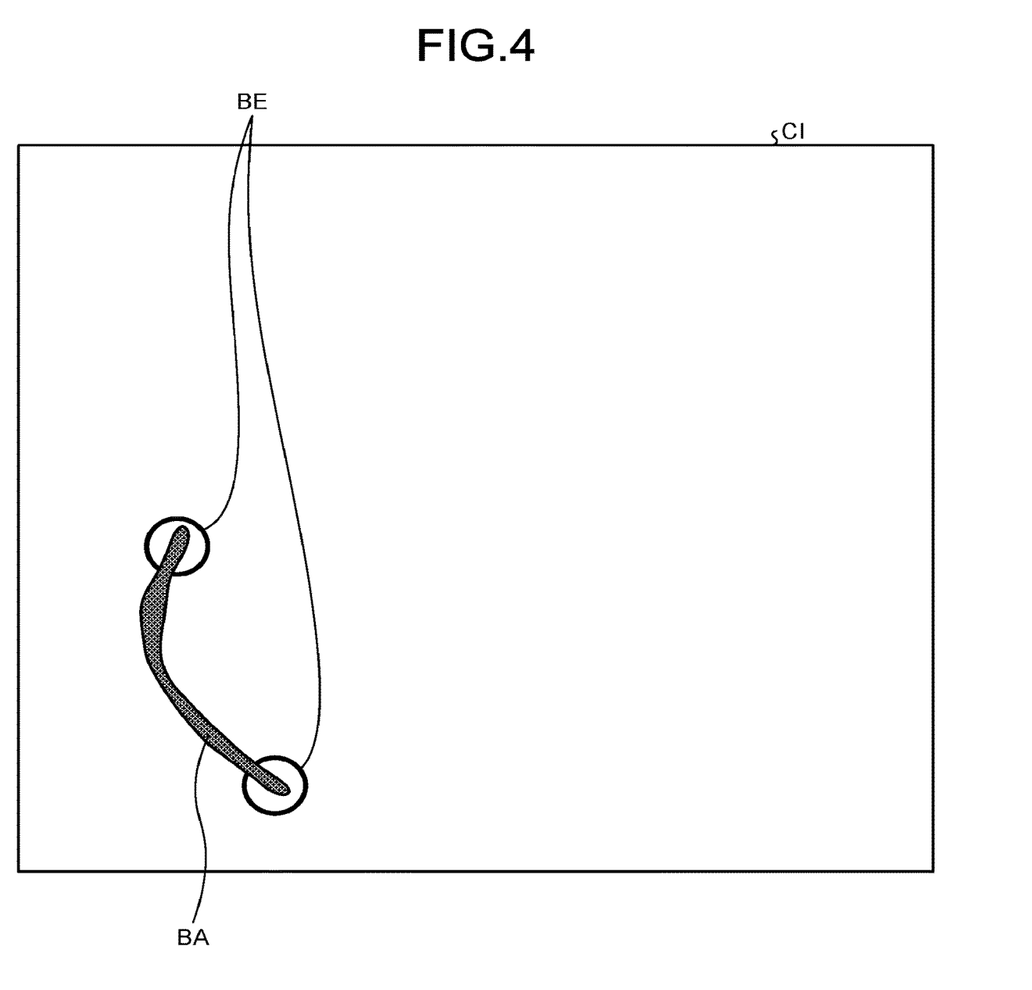
FIG. 4 is a schematic illustrating one example of an inflated balloon region in the catheter image according to the embodiment.

FIG. 4 is a schematic illustrating one example of the inflated balloon region BA in the catheter image CI. The processing circuitry 31 causes the setting function 313 to set regions near both ends of the region corresponding to the inflated balloon in the catheter image, as the areas to be searched. When the type of the inserted object is an inflated balloon, the area to be searched will be set to regions BE including both ends of the balloon region, as illustrated in FIG. 4.

When the type of the inserted object is a deflated balloon, the processing circuitry 31 causes the identifying function 312 to identify the wire region in the catheter image. The processing circuitry 31 then causes the setting function 313 to set a region near the wire including the region corresponding to the wire in the catheter image, as the area to be searched. The processing circuitry 31 may also set regions near both ends of the deflated balloon region, as the areas to be searched.

When the type of the inserted object is a plurality of balloons, the processing circuitry 31 causes the identifying function 312 to read at least one X-ray image generated in the past (past image), previously to the X-ray image, from the memory circuitry 23. The processing circuitry 31 causes the identifying function 312 to identify a dynamic balloon from the balloons, based on the X-ray image and the past image. A dynamic balloon is a balloon moving toward the periphery of the blood vessel, with the movement of the cardiac pulsations removed from the blood vessel region, for example. For example, the processing circuitry 31 identifies a dynamic balloon by taking subtraction of the past image from the X-ray image, and determining whether the movement has a cyclicity at one heartbeat. The processing circuitry 31 then causes the identifying function 312 to identify a wire region related to the dynamic balloon in the catheter image. The processing circuitry 31 then causes the setting function 313 to set a region near the wire region related to the dynamic balloon in the catheter image, as the area to be searched. The processing circuitry 31 may also set regions near both ends of the deflated balloon region as the areas to be searched.

Figure 5:
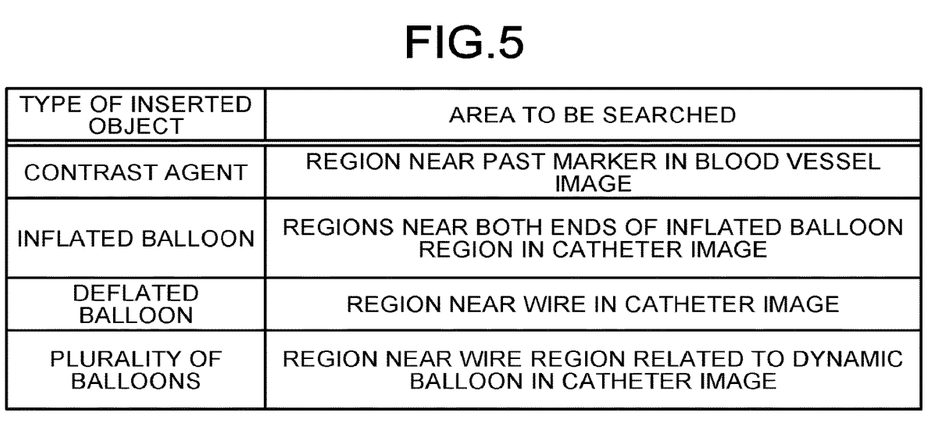
FIG. 5 is a schematic illustrating one example of a mapping table between a type of an inserted object and an area to be searched, according to the embodiment.

FIG. 5 is a schematic illustrating one example of a mapping table of a type of an inserted object and an area to be searched. The mapping table illustrated in FIG. 5 may be stored. The processing circuitry 31 causes the identifying function 312 and the setting function 313 to set the area where the marker is to be searched, in the manner explained at Step S201 to Step S205, in accordance with the mapping table illustrated in FIG. 5. For example, the processing circuitry 31 causes the identifying function 312 to set the area to be searched by matching the identified type against the mapping table. The processing circuitry 31 may also cause the identifying function 312 to set the area to be searched using a trained model taking the X-ray image and the identified type as inputs, and outputting the area to be searched in the X-ray image (hereinafter, referred to as a searched area setting model). The searched area setting model is trained in advance, based on the types. The searched area setting model is mapped to the type and stored in the memory circuitry 23.

Step S206

The processing circuitry 31 causes the marker detecting function 314 to search the area to be searched for the marker. For example, the processing circuitry 31 causes the marker detecting function 314 to detect a marker in the X-ray image using a trained model that takes an image corresponding to the area to be searched as an input, and that outputs a marker. If a marker is detected (Yes at Step S206), the process at Step S208 is performed.

Figure 6:
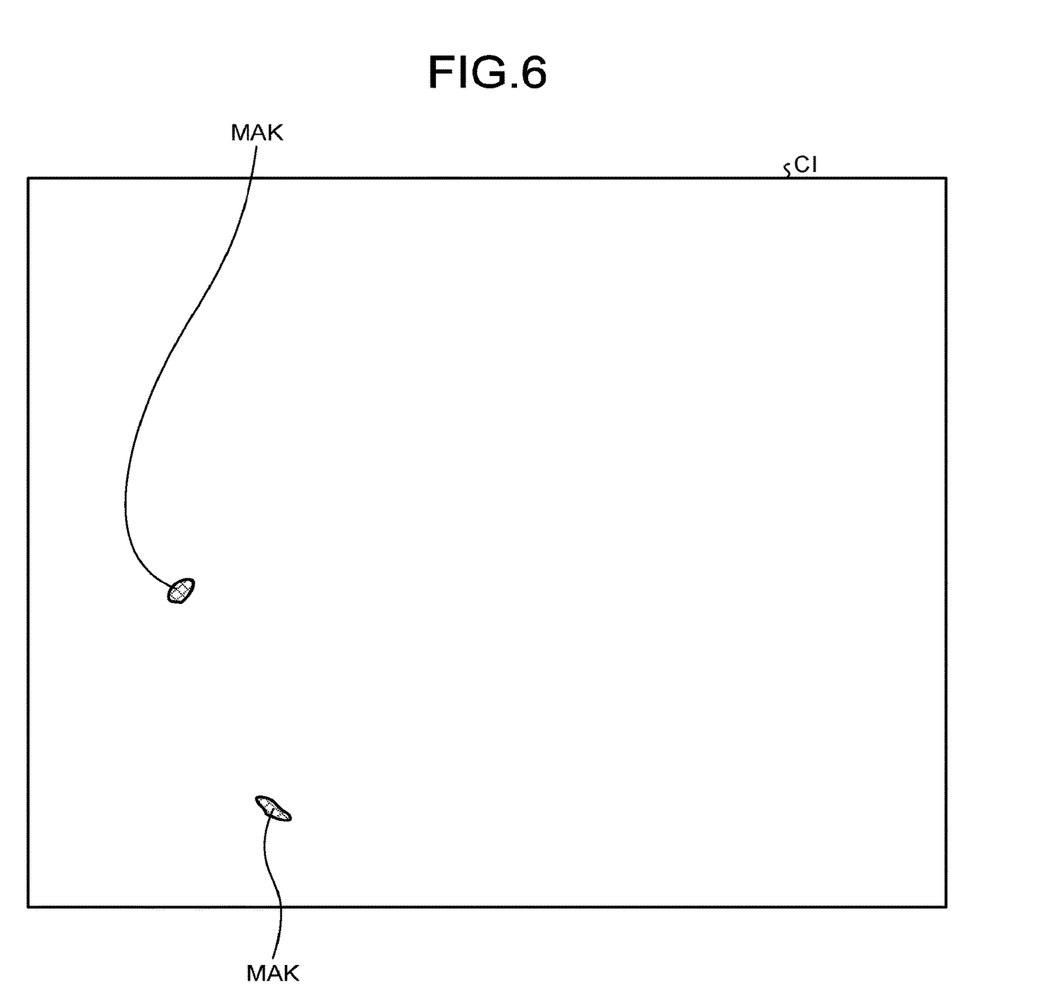
FIG. 6 is a schematic illustrating one example of the two markers in the catheter image when the type of the inserted object is an inflated balloon.

FIG. 6 is a schematic illustrating one example of the two markers MAK in the catheter image CI when the type of the inserted object is an inflated balloon. The processing circuitry 31 causes the marker detecting function 314 to search the area-to-be-searched BE illustrated in FIG. 4, for the marker. Because the area to be searched is restricted based on the type of the inserted object, the marker detectability and the marker detection accuracy are improved.

The processing circuitry 31 causes the marker detecting function 314 to detect a marker in the X-ray image by applying pattern matching to the image corresponding to the area to be searched, using the shape of the marker. The memory circuitry 23 stores therein a mapping table of the model number of the balloon inserted in the subject P, and the shape of the marker corresponding to the model number (hereinafter, referred to as a shape mapping table). The processing circuitry 31 causes the marker detecting function 314 to match the model number of the balloon, entered by the operator via the input interface 27, to the shape mapping table, before the intervention treatment. Through this matching, the processing circuitry 31 identifies the shape of the marker provided to the catheter to be inserted into the subject P. The processing circuitry 31 then detects the marker in the X-ray image by applying pattern matching to the image corresponding to the area to be searched, using the identified shape of the marker. In this manner, the marker detection accuracy is improved.

If no marker is detected (No at Step S206), the process at Step S207 is performed. For example, if the presence of the contrast agent is identified in the X-ray image, but no marker is detected from the area to be searched, the display 29 may cause the marker detecting function 314 to display information for reducing the concentration of the contrast agent on the display 29. The information for reducing the concentration of the contrast agent is information for reducing the speed at which the contrast agent is injected, for example. An example of the information for reducing the speed at which the contrast agent is injected may be a number indicating a percentage less than 100%, for example, 80%.

If the presence of contrast agent is not identified in the X-ray image, and no marker is detected from the area to be searched, the processing circuitry 31 causes the identifying function 312 to identify the degree by which the inserted object is blurred in the X-ray image. Specifically, the processing circuitry 31 calculates the degree of blur by dividing the number of pixels in the marker by the speed at which the marker moves between the frames, for example. The processing circuitry 31 may also identify the degree of blur by calculating the difference between the past image and the current X-ray image. If the degree of blur is smaller than one, the display 29 causes the identifying function 312 to display a warning to increase the frame rate related to the X-ray exposure, or to display a frame rate at which the blur can be resolved, based on the degree of blur. The frame rate where the blur can be resolved is indicated as a percentage indicating an increase from the current frame rate, for example.

If the presence of contrast agent is not identified in the X-ray image, and no marker is detected from the area to be searched, the processing circuitry 31 may cause the control function 311 to change an X-ray condition related to the X-ray in such a manner that the X-ray dose is increased, or to change the X-ray filter related to the X-ray. At this time, the display 29 may display the current X-ray condition and the X-ray condition after the change, or the current X-ray filter and the X-ray filter after the change. The operator may then select the X-ray condition after the change or the X-ray filter after the change via the input interface 27.

Step S207

The processing circuitry 31 causes the control function 311 to control the image processing circuitry 25 to output the X-ray image, onto the display 29. The display 29 then displays the X-ray image.

Step S208

The image processing circuitry 25 then superimposes the detected marker over the X-ray image. In this manner, the image processing circuitry 25 generates a superimposed image. The image processing circuitry 25 may change the hue or the contrast of the structures of the catheter, including the marker, in the superimposed image. In other words, the image processing circuitry 25 may emphasize the structures associated with the catheter in the superimposed image. The image processing circuitry 25 then detects the position of the marker in the superimposed image. The image processing circuitry 25 then performs a coordinate conversion to the superimposed image so that the detected position of the marker comes to the position at the center of the display 29. If the pixel value of the marker detected in the X-ray image is equal to or greater than a threshold related to the pixel values (hereinafter, referred to as a marker threshold), the processing circuitry 31 may cause the control function 311 to change the X-ray condition related to the X-ray or the X-ray filter that is related to the X-ray so as to reduce the X-ray dose. At this time, the display 29 may display the current X-ray condition and the X-ray condition after the change, or the current X-ray filter and the X-ray filter after the change. The operator may then select the X-ray condition after the change or the X-ray filter after the change via the input interface 27.

Step S209

The image processing circuitry 25 outputs the superimposed image applied with the coordinate conversion onto the display 29. The display 29 then displays the superimposed image applied with the coordinate conversion. In other words, the display 29 displays the superimposed image in such a manner that the position of the marker in the superimposed image is fixed to the center of the screen.

Step S210

If the examination has not been completed yet (No at Step S210), the processes at Step S201 to Step S210 is repeated. If the examination has been completed (Yes at Step S210), the marker detection process is ended.

The X-ray diagnostic apparatus 100 according to the embodiment described above generates an X-ray image one after another, based on an output of the X-ray detector 16 that is positioned in a manner facing the X-ray tube 12 for generating an X-ray, and that detects the X-rays; identifies the type of the inserted object inside the subject P in the X-ray image by performing an image recognition process to the X-ray image; sets the area where the marker of the inserted object is to be searched, based on the type identified in the X-ray image; and detects the marker in the X-ray image, by searching the set area to be searched for the marker. In this manner, because the X-ray diagnostic apparatus 100 according to the embodiment can set the area where the marker is to be searched based on the type of the inserted object inside the subject P, the marker detection accuracy is improved, and false detections of the markers can be reduced. In other words, with the X-ray diagnostic apparatus 100 according to the embodiment, it is possible to reduce the false positives or false negatives of the marker detections, so that it is possible to improve the throughput and the operability in the intervention treatment, for example.

Figure 7:
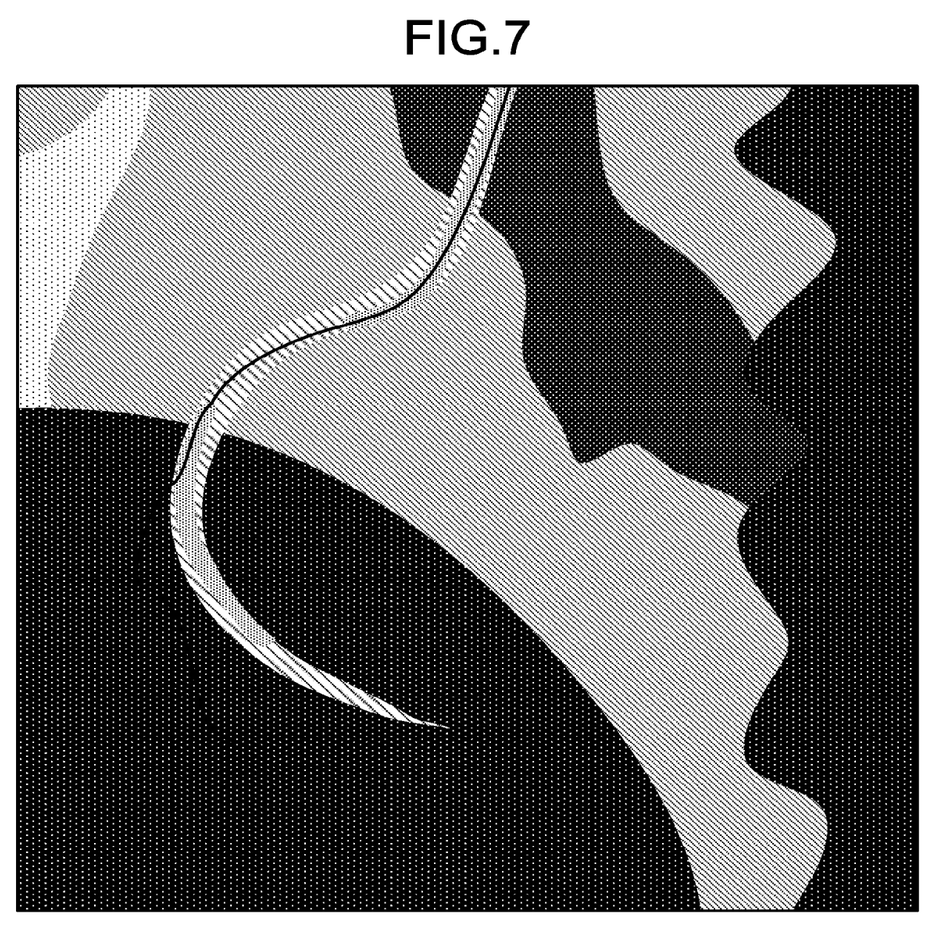
FIG. 7 is a schematic illustrating one example of an X-ray image related to an inflated balloon according to the embodiment.

FIG. 7 is a schematic illustrating one example of an X-ray image related to an inflated balloon. As illustrated in FIG. 7, an inflated balloon having been expanded and injected with contrast agent (hereinafter, referred to as a contrast balloon) makes it difficult to detect the markers. Therefore, in the X-ray diagnostic apparatus 100 according to the embodiment, when the type of the inserted object is identified as an inflated balloon, regions near both ends of the inflated balloon region are set as the areas to be searched. Specifically, to begin with, the X-ray diagnostic apparatus 100 identifies, when the type of the inserted object is identified as an inflated balloon, the balloon region BA in the X-ray image. Because the contrast balloon has been injected with contrast agent, the contrast balloon can be detected relatively easily, compared with a deflated balloon. The X-ray diagnostic apparatus 100 then sets the regions BE near both ends of the balloon region BA as the areas to be searched. These areas to be searched are set by taking advantage of the fact that the balloon has markers on both ends. In this manner, with the X-ray diagnostic apparatus 100, it is possible to reduce the chances of missed marker detections, so that it is possible to improve the marker detection accuracy.

Figure 8:
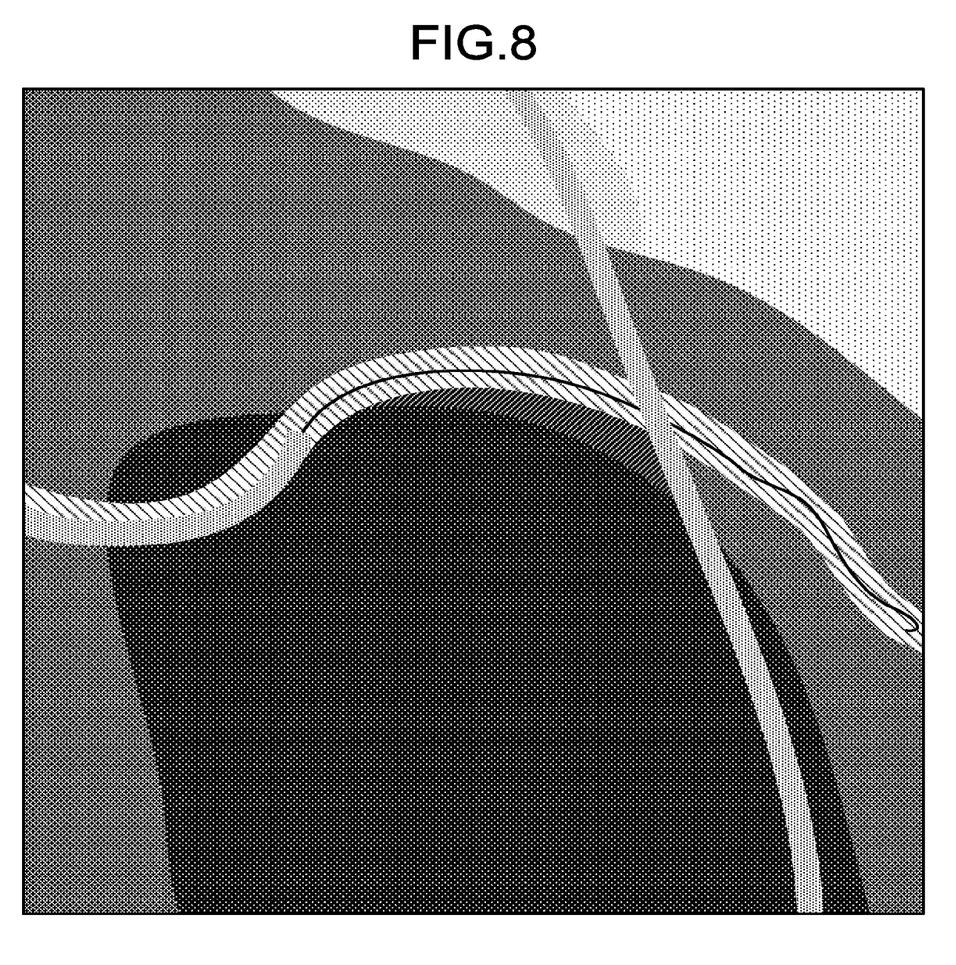
FIG. 8 is a schematic illustrating one example of an X-ray image related to a deflated balloon according to the embodiment.

FIG. 8 is a schematic illustrating one example of an X-ray image related to a deflated balloon. As illustrated in FIG. 8, there are chances for a region with a high X-ray attenuation coefficient, such as a region corresponding to a bone, in the X-ray image to be falsely detected as a marker. With the X-ray diagnostic apparatus 100 according to the embodiment, when the type of the inserted object is identified as a deflated balloon, a region near the wire region related to the deflated balloon is set as the area to be searched. Specifically, when the type of the inserted object is identified as a deflated balloon, the X-ray diagnostic apparatus 100 can identify the wire region related to the balloon in the X-ray image, and set the region near the wire region as the area to be searched. In other words, because a region with a high X-ray attenuation coefficient, such as a region corresponding to a bone, is excluded from the X-ray image, and the area to be searched is set near the wire, it is possible to improve the marker detectability. In the manner described above, because the X-ray diagnostic apparatus 100 according to the embodiment can reduce the chances for a region with a high X-ray attenuation coefficient to be falsely detected as a marker, it is possible to improve the marker detection accuracy.

Figure 9:
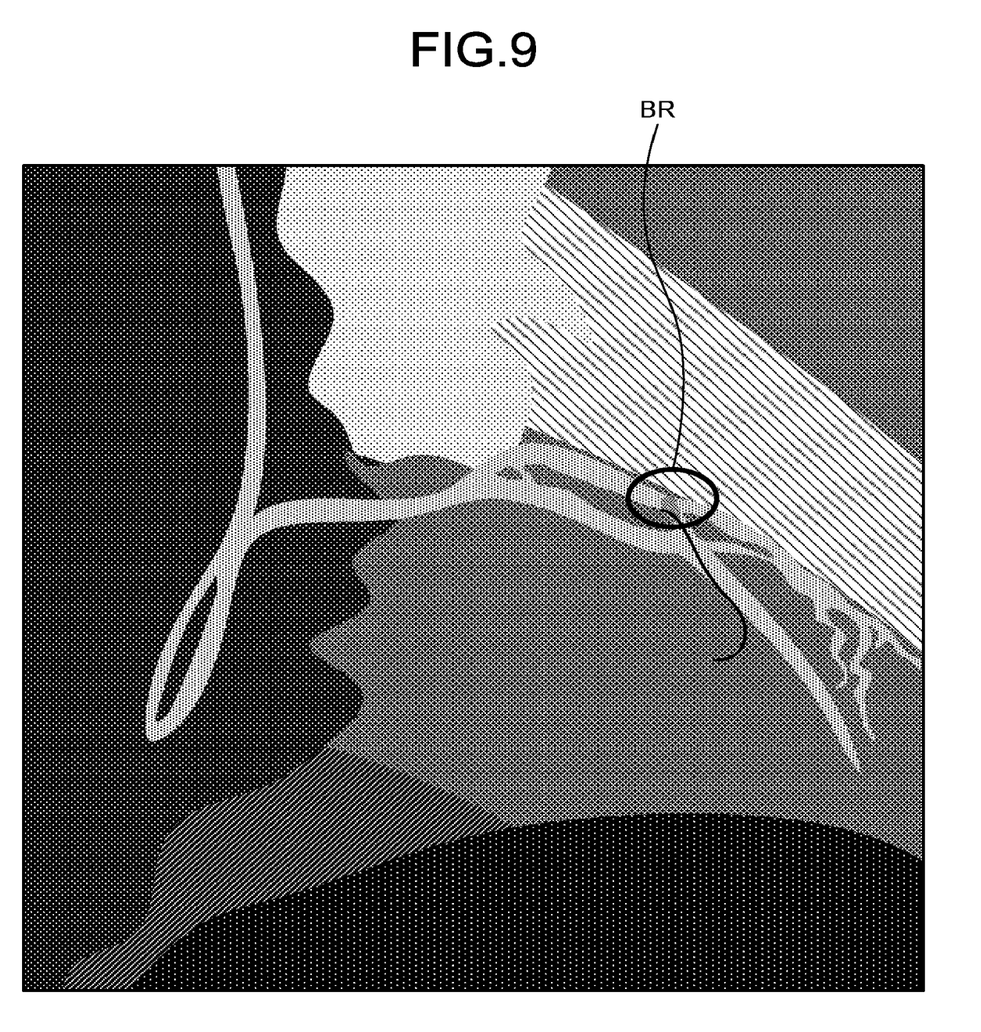
FIG. 9 is a schematic illustrating one example of an X-ray image with contrast agent injected, as the inserted object in the subject P according to the embodiment.

FIG. 9 is a schematic illustrating one example of an X-ray image with contrast agent injected, as the inserted object inside the subject P. As illustrated in FIG. 9, there are chances for a region with a high X-ray attenuation coefficient, e.g., a branch section BR of a blood vessel or an overlapping section of blood vessels, to be falsely detected as a marker in the X-ray image. Therefore, when the type of the inserted object is identified as contrast agent, the X-ray diagnostic apparatus 100 according to the embodiment sets a region near a marker in a past X-ray image captured at the same cardiac phase as that of the X-ray image, in the blood vessel region in the X-ray image, as the area to be searched, except for a branch section of the blood vessel and an overlapping section where the blood vessels overlap each other in the direction in which the X-ray is projected. Specifically, when the type of the inserted object is identified as contrast agent, the X-ray diagnostic apparatus 100 identifies a branch section of a blood vessel and an overlapping section where blood vessels overlap each other in the direction in which the X-ray is projected, in the blood vessel region in the X-ray image. In this manner, it is possible to exclude the regions with a high contrast agent concentration in advance before a marker detection is carried out. The X-ray diagnostic apparatus 100 then excludes the branch section and the overlapping section from the blood vessel region, and sets a region near a marker in a past X-ray image captured at the same cardiac phase as that of the X-ray image, as the area to be searched. The area to be searched is set using a past marker in a past X-ray image captured substantially at the same cardiac phase as that of the current X-ray image. In this manner, with the X-ray diagnostic apparatus 100, it is possible to reduce missed or false marker detections, so that it is possible to improve the marker detection accuracy.

Furthermore, with the X-ray diagnostic apparatus 100 according to the embodiment, when the type of the inserted object is identified as a plurality of balloons, a region near the wire region related to a dynamic balloon, among the balloons, is set as the area to be searched. Specifically, when the type of the inserted object is identified as a plurality of balloons, the X-ray diagnostic apparatus 100 identifies a dynamic balloon from the balloons, based on the X-ray image and at least one X-ray image generated previously to the X-ray image. The X-ray diagnostic apparatus 100 then identifies the wire region related to the dynamic balloon in the X-ray image, and sets a region near the wire region as the area to be searched. In this manner, when a plurality of balloons are inserted into the subject P, because a dynamic balloon is moving, it is possible to exclude a region related to a static balloon that remains unmoving between frames, among the balloons. Therefore, the X-ray diagnostic apparatus 100 can reduce the false marker detections, resultant of falsely identifying a marker pair for the balloon, so that it is possible to improve the marker detection accuracy.

Furthermore, the X-ray diagnostic apparatus 100 according to the embodiment generates a superimposed image in which the detected marker is superimposed over the X-ray image, and displays the superimposed image with the position of the marker in the superimposed image fixed to the center of the screen of the display 29. At this time, the structures of the catheter, including the marker and the balloon, may be displayed in an emphasized manner, e.g., in a different hue or different contrast, in the superimposed image displayed on the display 29. In this manner, it is possible to improve the throughput and the operability in the intervention treatment.

Furthermore, with the X-ray diagnostic apparatus 100 according to the embodiment, when the presence of the contrast agent is identified in the X-ray image, and no marker is detected from the area to be searched, the information for reducing the concentration of the contrast agent is displayed on the display 29. Furthermore, when the presence of contrast agent is not identified in the X-ray image, and no marker is detected from the area to be searched, the X-ray diagnostic apparatus 100 identifies the degree by which the inserted object is blurred in the X-ray image, and displays a warning to increase the frame rate related to the X-ray exposure, or a frame rate at which the blur can be resolved, based on the degree of blur. Furthermore, when the presence of contrast agent is not identified in the X-ray image, and no marker is detected from the area to be searched, the X-ray diagnostic apparatus 100 changes the X-ray condition related to the X-ray, or the X-ray filter related to the X-ray, in such a manner that the X-ray dose is increased. In this manner, it is possible to present some information for resolving missed marker detections to the operator, so that the marker detection accuracy can be improved. Furthermore, when the pixel value of the marker detected in the X-ray image is equal to or greater than a marker threshold, the X-ray diagnostic apparatus 100 may change the X-ray condition related to the X-ray, or the X-ray filter related to the X-ray, in such a manner that the X-ray dose is reduced. In this manner, it is possible to reduce the exposure of the subject P to the X-ray radiation.

First Modification

The marker inserted in the subject P moves in synchronization with the heartbeat of the subject P. By contrast, the diaphragm of the subject P moves in synchronization with breathing of the subject P. Therefore, the detected marker sometimes overlaps with at least one of a bone region and a diaphragm region in the X-ray image of the subsequent frame, or in the X-ray image subsequent to a plurality of frames. A first modification is intended to move the position of the X-ray detector 16 with respect to the subject P when the detected marker overlaps with at least one of a bone region and a diaphragm region. A process according to the first modification is performed immediately previously to Step S201 in the marker detection process illustrated in FIG. 2, for example.

The processing circuitry 31 causes the identifying function 312 to identify a bone region and a diaphragm region in the X-ray image. The bone region and diaphragm region identifications are performed, for example, using the 2D-3D aligning program. When at least one of the bone region and the diaphragm region overlaps with the marker, the processing circuitry 31 causes the control function 311 to move the position of the X-ray detector 16 with respect to the subject P. Specifically, the processing circuitry 31 actuates the C arm 15 via the C arm/couchtop mechanism controller circuitry 19, and moves the position of the X-ray detector 16 so that the at least one of the bone region and the diaphragm region does not overlap with the detected marker.

With the X-ray diagnostic apparatus 100 according to the first modification of the embodiment described above, a bone region and a diaphragm region are identified in the X-ray image, and when at least one of the bone region and the diaphragm region overlaps with a marker, the position of the X-ray detector 16 with respect to the subject P is moved. In this manner, it is possible to avoid overlapping of at least one of the bone region and the diaphragm region with the detected marker, in the X-ray image subsequent to the current frame. Therefore, it is possible to reduce false and missed marker detections due to the overlapping of at least one of the bone region and the diaphragm region with the marker, so that it is possible to improve the marker detection accuracy.

Second Modification

A second modification is intended, when it is identified that a region representing a wire in the X-ray image (hereinafter, referred to as a wire region) is in contact with an end of the X-ray image, to move the C arm 15 in such a manner that the wire comes inside of the display area of the display 29.

The processing circuitry 31 causes the identifying function 312 to identify whether the wire region is in contact with an end of the X-ray image, in the X-ray image. This identification may also be performed by the image processing circuitry 25. The processing circuitry 31 causes the control function 311 to actuate the C arm 15 via the C arm/couchtop mechanism controller circuitry 19 to move the C arm 15 in such a manner that the wire comes inside of the display area of the display 29. In this manner, it is possible to reduce missed marker detections.

When the technical idea disclosed in this embodiment is implemented as a marker detecting method, the marker detecting method generates an X-ray image one after another, based on a detected X-ray, identifies the type of the inserted object inside the subject P in the X-ray image by performing an image recognition process to the X-ray image, sets the area where the marker of the inserted object is to be searched based on the type identified in the X-ray image, and detects a marker in the X-ray image by searching the area to be searched for the marker. Because the sequence of and the effects achieved by the marker detecting method are the same as those disclosed in the embodiment, explanations thereof will be omitted.

When the technical idea disclosed in this embodiment is implemented as a marker detection processing program, a computer is caused to implement generating an X-ray image one after another, based on a detected X-ray, identifying the type of an inserted object inside the subject P in the X-ray image, by performing an image recognition process to the X-ray image, setting the area where the marker of the inserted object is to be searched based on the type identified in the X-ray image, and detecting a marker in the X-ray image, by searching the area to be searched for the marker.

For example, the marker detection processing program may be implemented by installing the computer program on a computer in the X-ray diagnostic apparatus 100, and loading the computer program onto the memory. The computer program capable of causing a computer to execute this algorithm may also be provided in a manner stored in a recording medium such as a magnetic disk (such as a hard disk), an optical disc (a compact disc read-only memory (CD-ROM), or a digital versatile disc (DVD)), or a semiconductor memory. For example, a computer-readable non-transitory recording medium stores therein a marker detecting program for causing a computer to implement detection of a marker in the X-ray image, by generating an X-ray image one after another, based on a detected X-ray, identifying the inserted object inside the subject in the X-ray image by performing an image recognition process to the X-ray image, setting an area where the marker is to be searched based on the inserted object identified in the X-ray image, and searching the area to be searched for the marker. Because the sequence of and the effects achieved by the marker detecting program are the same as those disclosed in the embodiment, explanations thereof will be omitted.

According to the embodiment and the modifications thereof explained above, it is possible to improve the accuracy of the marker detections.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray tube configured to generate an X-ray;
an X-ray detector that is positioned in a manner facing the X-ray tube, and configured to detect the X-ray;
image generating circuitry configured to generate an X-ray image, based on an output of the X-ray detector; and processing circuitry configured to:
  identify an inserted object inside a subject in the X-ray image, by performing an image recognition process on the X-ray image;
  set an area to be searched for a marker in the X-ray image, based on the identified inserted object, and
  detect the marker in the X-ray image, by searching the get area to be searched for the marker.

2. The X-ray diagnostic apparatus according to claim 1, wherein
  the image processing circuitry is further configured to generate a superimposed image in which the detected marker is superimposed over the X-ray image, and
  the X-ray diagnostic apparatus further comprises a display configured to display the superimposed image with a position of the marker in the superimposed image fixed to a center of a screen.

3. The X-ray diagnostic apparatus according to claim 1, wherein the processing circuitry is further configured to, when the inserted object is identified as an inflated balloon, set regions near both ends of a region of the balloon as the area to be searched.

4. The X-ray diagnostic apparatus according to claim 1, wherein the processing circuitry is further configured to, when the inserted object is identified as a deflated balloon, set a region near a wire region related to the balloon as the area to be searched.

5. The X-ray diagnostic apparatus according to claim 1, wherein the processing circuitry is further configured to, when the inserted object is identified as a plurality of balloons, set a region near a wire region related to a dynamic balloon, among the plurality of balloons, as the area to be searched.

6. The X-ray diagnostic apparatus according to claim 1, wherein the processing circuitry is further configured to, when the inserted object is identified as contrast agent, set a region near the marker in a past X-ray image captured at a same cardiac phase as that of the X-ray image, in a region resultant of excluding a branch section of a blood vessel and an overlapping section where blood vessels overlap each other in a direction in which the X-ray is projected, from a blood vessel region in the X-ray image, as the area to be searched.

7. The X-ray diagnostic apparatus according to claim 6, further comprising a display configured to display, when the marker has not been detected in the area to be searched, information for reducing concentration of contrast agent.

8. The X-ray diagnostic apparatus according to claim 1, wherein
  the processing circuitry is further configured to identify a degree by which the inserted object is blurred in the X-ray image, and
  the X-ray diagnostic apparatus further comprises a display configured to display a warning to increase a frame rate related to an X-ray exposure, or a frame rate enabling blur to be resolved, based on the degree of blur.

9. The X-ray diagnostic apparatus according to claim 1, wherein the processing circuitry is further configured to, when the marker has not been detected in the area to be searched, change an X-ray condition related to the X-ray, or an X-ray filter related to the X-ray, in such a manner that a dose of the X-ray is increased.

10. The X-ray diagnostic apparatus according to claim 1, wherein the processing circuitry is further configured to:
  identify a bone region and a diaphragm region in the X-ray image, and
  move a position of the X-ray detector with respect to the subject when at least one of the bone region and the diaphragm region overlaps with the marker.

11. The X-ray diagnostic apparatus according to claim 1, wherein, the processing circuitry is further configured to, when a pixel value indicating the marker is equal to or greater than a threshold, change an X-ray condition related to the X-ray, or an X-ray filter related to the X-ray, in such a manner that a dose of the X-ray is reduced.

12. A marker detecting method, comprising:
  generating an X-ray image based on a detected X-ray;
  identifying an inserted object inside a subject in the X-ray image, by performing an image recognition process on the X-ray image;
  setting an area to be searched for a marker in the X-ray image, based on the identified inserted object; and
  detecting the marker in the X-ray image, by searching the set area to be searched for the marker.

13. A non-transitory computer readable medium comprising instructions that cause a computer to execute:
  generating an X-ray image based on a detected X-ray;
  identifying an inserted object inside a subject in the X-ray image, by performing an image recognition process on the X-ray image;
  setting an area to be searched for a marker in the X-ray image, based on the identified inserted object; and
  detecting the marker in the X-ray image, by searching the set area to be searched for the marker.

* * * * *